United States Patent
Yamamoto et al.

(10) Patent No.: US 11,370,747 B2
(45) Date of Patent: Jun. 28, 2022

(54) METHOD FOR PRODUCING AMIDE COMPOUND

(71) Applicant: CHUBU UNIVERSITY EDUCATIONAL FOUNDATION, Kasugai (JP)

(72) Inventors: Hisashi Yamamoto, Kasugai (JP); Wataru Muramatsu, Kasugai (JP); Tomohiro Hattori, Kasugai (JP); Yasushi Shimoda, Kasugai (JP); Hiroaki Tsuji, Kasugai (JP)

(73) Assignee: CHUBU UNIVERSITY EDUCATIONAL FOUNDATION, Aichi (JP)

( * ) Notice: Subject to any disclaimer, the term of this patent is extended or adjusted under 35 U.S.C. 154(b) by 0 days.

(21) Appl. No.: 16/607,443

(22) PCT Filed: Apr. 25, 2018

(86) PCT No.: PCT/JP2018/016767
§ 371 (c)(1),
(2) Date: Oct. 23, 2019

(87) PCT Pub. No.: WO2018/199147
PCT Pub. Date: Nov. 1, 2018

(65) Prior Publication Data
US 2020/0131117 A1    Apr. 30, 2020

(30) Foreign Application Priority Data

Apr. 25, 2017  (JP) .............. JP2017-086270

(51) Int. Cl.
| | | |
|---|---|---|
| *C07C 231/02* | (2006.01) | |
| *C07C 231/12* | (2006.01) | |
| *C07C 269/06* | (2006.01) | |
| *B01J 31/02* | (2006.01) | |
| *B01J 31/36* | (2006.01) | |
| *C07C 237/12* | (2006.01) | |
| *C07C 271/20* | (2006.01) | |
| *C07C 271/22* | (2006.01) | |

(52) U.S. Cl.
CPC .......... *C07C 231/02* (2013.01); *C07C 231/12* (2013.01); *C07C 269/06* (2013.01); *B01J 31/0212* (2013.01); *B01J 31/36* (2013.01); *B01J 2531/58* (2013.01); *C07C 237/12* (2013.01); *C07C 271/20* (2013.01); *C07C 271/22* (2013.01)

(58) Field of Classification Search
None
See application file for complete search history.

(56) References Cited

FOREIGN PATENT DOCUMENTS

| | | | | |
|---|---|---|---|---|
| EP | 3466922 A1 | * | 4/2019 | ........... C07C 231/02 |
| WO | 2009/060843 A1 | | 5/2009 | |
| WO | WO-2017204144 A1 | * | 11/2017 | ........... C07C 235/08 |
| WO | 2018/199146 A1 | | 11/2018 | |

OTHER PUBLICATIONS

Allen ("Direct amide formation from unactivated carboxylic acids and amines" ChemComm 2012, 48, p. 666-668, including Supporting Information (SI) p. 1-44) (Year: 2012).*
Ohshima ("Sodium Methoxide: a simple but highly efficient catalyst for the direct amidation of esters" ChemComm 2012, 48, p. 5434-5436, including Supporting Information (SI) p. S1-S19) (Year: 2012).*
Isidro-Llobet ("Amino Acid-Protecting Groups" Chem. Rev. 2009, 109, p. 2455-2504) (Year: 2009).*
Han ("Catalytic Ester-Amide Exchange Using Group (IV) Metal Alkoxide-Activator Complexes" J. Am. Chem. Soc., 2005, 127, p. 10039-10044) (Year: 2005).*
Han ("Catalytic Ester-Amide Exchange Using Group (IV) Metal Alkoxide-Activator Complexes" J. Am. Chem. Soc., 2005, 127, p. 10039-10044, including Supporting Information (SI), p. S1-S31) (Year: 2005).*
Roos ("Palladium Catalyzed Transprotection of Allyloxycarbonyl-Protected Amines: Efficient One-Pot Formation of Amides and Dipeptides" J. Org. Chem. 1995, 60, p. 1733-1740) (Year: 1995).*
Kinoshita ("The Cinnamyloxycarbonyl Group as a New Amino-Protecting Group" Chemistry Letters, 1985, p. 515-518) (Year: 1985).*
Minami ("1-Isopropylallyloxycarbonyl (IPAoc) as a protective group of amines and its deprotection catalyzed by palladium-phosphine complex" Tetrahedron Letters, 1987, 28(24), p. 2737-2740) (Year: 1987).*
International Search Report dated Jul. 24, 2018 corresponding to PCT/JP2018/016767 filed Apr. 25, 2018; 2 pages. English translation.
Davie, Elizabeth A. Colby et al., "Asymmetric Catalysis Mediated by Synthetic Peptides," *Chem Rev.* (2007; published on Web Dec. 12, 2007) 107:5759-5812.
De Figueiredo, Renata Marcia et al., "Nonclassical Routes for Amide Bond Formation," *Chem. Rev.* (Sep. 22, 2016) 116:12029-12122.
Dunetz, Joshua R. et al., "Large-Scale Applications of Amide Coupling Reagents for the Synthesis of Pharmaceuticals," *Organic Process Research & Development* (2016; published Nov. 15, 2015) 20:140-177.
El-Faham, Ayman et al., "Peptide Coupling Reagents, More than a Letter Soup," *Chem. Rev.* (Aug. 26, 2011) 111:6557-6602.
Montalbetti, Christian A. G. N. et al., "Amide bond formation and peptide coupling," *Tetrahedron* (2005; available online Sep. 19, 2005) 61:10827-10852.

(Continued)

*Primary Examiner* — Amy C Bonaparte
(74) *Attorney, Agent, or Firm* — Mintz, Levin, Cohn, Ferris, Glovsky and Popeo, P.C.

(57) ABSTRACT

Provided is a novel method for producing amide compounds at high stereochemical selectivities. The method according to the present invention for producing amide compounds is provided with an amidation step for reacting, in the presence of a catalyst comprising a metal compound, an amino compound with an aminoester compound represented by general formula (1) to amidate the ester group in the aminoester compound.

10 Claims, No Drawings

(56) References Cited

OTHER PUBLICATIONS

Nilsson, Bradley L. et al., "Chemical Synthesis of Proteins," *Annu. Rev. Biophys. Biomol. Struct.* (2005; first published online as a Review in Advance Jan. 24, 2005) 34:91-118.

Tsuji, Hiroaki et al., "Hydroxy-Directed Amidation of Carboxylic Acid Esters Using a Tantalum Alkoxide Catalyst," *J. Am. Chem. Soc.* (Oct. 16, 2016) 138:14218-14221.

International Search Report dated Jul. 30, 2019 corresponding to PCT/JP2019/0177867 filed Apr. 25, 2019; 1 page. English translation.

Supplementary European Search Report dated Dec. 10, 2020 corresponding to EP18789973.7 filed Apr. 25, 2018; 5 pages.

Bode, Jeffrey W. et al., "Chemoselective Amide Ligations by Decarboxylative Condensations of N-Alkylhydroxylamines and α-Ketoacids," *Angew. Chem. Int. Ed.* (Published online Jan. 17, 2006) 45:1248-1252.

Colby Davie, Elizabeth A. et al., "Asymmetric Catalysis Mediated by Synthetic Peptides," *Chem. Rev.* (Published on Web Dec. 12, 2007) 107:5759-5812.

Fang, Jiang Bao et al., "Tantalum pentachloride as a coupling agent for stereohindered amide bond formation," *Inoorganica Chimica ACTA* (Jul. 1, 2004) 357(9):2415-2426.

Schnölzer, Martina et al., "Constructing Proteins by Dovetailing Unprotected Synthetic Peptides: Backbone-Engineered HIV Protease," *Science* (Apr. 10, 1992) 256:221-225.

\* cited by examiner

METHOD FOR PRODUCING AMIDE COMPOUND

FIELD

The present invention pertains to a method for producing an amide compound.

BACKGROUND

Conventionally, amide compounds represented by peptides have been used in a wide variety of fields, including pharmaceuticals, cosmetics, and functional foods. Development of synthetic methods thereof has been diligently pursued as an important research goal in synthetic chemistry (NPTL 1 to 6). However, there are not many catalysts that are effective for the amidation reaction, which is the most important reaction in peptide synthesis. Therefore, it is necessary to use an equivalent reagent that forms by-products, and thus, peptide synthesis, which involves repeating multi-stage reactions, is extremely inefficient from the perspective of atom economy (atomic yield). The amount of by-products is large, and there are few effective purification means. As a result, the cost of disposal of by-products and purification constitutes most of the necessary costs for peptide synthesis, and is the largest obstacle to development in this field.

CITATION LIST

Non-Patent Literature

[NPL 1] Annu. Rev. Biophys. Biomol. Struct., 2005, 34, 91-118
[NPL 2] Tetrahedron, 2005, 6, 10827-10852
[NPL 3] Chem. Rev., 2007, 107, 5759-5812
[NPL 4] Chem. Rev., 2011, 111, 6557-6602
[NPL 5] Org. Process Res. Dev., 2016, 20(2), 140-177
[NPL 6] Chem. Rev., 2016, 116, 12029-12122

SUMMARY

Technical Problem

In peptide synthesis, which uses amino acids or derivatives thereof as starting materials, it is desirable for the amidation reaction to proceed with high stereoselectivity. Enzyme reactions in the body are examples of highly stereoselective amidation reactions. For example, in the body, peptides are synthesized with extremely high stereoselectivity through sophisticated use of enzymes and hydrogen bonds. However, enzyme reactions are not suitable for mass production, requiring excessive financial and time costs when applied to synthetic chemistry.

In synthetic chemistry, amidation reactions using catalysts have been examined, but in conventional means, the amide bond is formed primarily through the method of activating carboxylic acid, such that racemization occurs quickly, whereby synthesizing a peptide with high stereoselectivity is difficult. Thus, currently in synthetic chemistry, no method for synthesizing a peptide with high stereoselectivity using a catalyst has been made practicable. Amid this background, development of a highly stereochemically selective amidation reaction is desired.

Under these circumstances, the object of the present invention is to provide a novel method for producing an amide compound with highly stereochemical selectivity.

The present inventors engaged in keen examination in order to achieve the above object. As a result, they discovered that a highly stereochemically selective amidation reaction can be achieved by a novel method for producing an amide compound comprising an amidation step of reacting, in the presence of a catalyst comprising a metal compound, an amino compound with an aminoester compound represented by the general formula (1) below to amidate an ester group of the aminoester compound. The present invention was completed through further repeated examinations based on these findings.

[Chem 1]

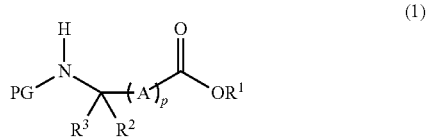

(1)

In Formula (1), group $R^1$ represents an optionally substituted aliphatic group, an optionally substituted aromatic group, an optionally substituted alicyclic group, or an optionally substituted heterocyclic group. Groups $R^2$ and $R^3$ each independently represent a hydrogen atom, a halogen atom, a hydroxyl group, an optionally substituted aliphatic group, an optionally substituted aromatic group, an optionally substituted alicyclic group, or an optionally substituted heterocyclic group. Group PG represents an amino group-protecting group. A represents a linear or branched optionally substituted alkyl group having 1 to 3 carbon atoms. p is 0 or 1.

Basically, the present invention includes the following embodiments.

Item 1. A method for producing an amide compound, comprising an amidation step for reacting, in the presence of a catalyst comprising a metal compound, an amino compound with an aminoester compound represented by general formula (1) below to amidate the ester group in the aminoester compound:

[Chem 2]

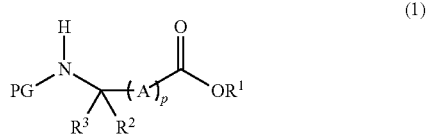

(1)

where group $R^1$ represents an optionally substituted aliphatic group, an optionally substituted aromatic group, an optionally substituted alicyclic group, or an optionally substituted heterocyclic group, group $R^2$ and group $R^3$ each independently represent a hydrogen atom, a halogen atom, a hydroxyl group, an optionally substituted aliphatic group, an optionally substituted aromatic group, an optionally substituted alicyclic group, or an optionally substituted heterocyclic group, group PG represents an amino group-protecting group, A represents a linear or branched optionally substituted alkyl group having 1 to 3 carbon atoms, and p is 0 or 1.

Item 2. The method for producing an amide compound according to item 1, further comprising a deprotection step wherein after the amidation step, in the obtained amide compound, the protecting group PG derived from the aminoester compound represented by general formula (1) is deprotected to obtain a converted amino group.

Item 3. The method for producing an amide compound according to item 2, further comprising an amidation step for reacting, in the presence of a catalyst comprising a metal compound, the amide compound having the amino group obtained in item 2 with an aminoester compound represented by general formula (1) to amidate the ester group of the aminoester compound.

Item 4. The method for producing an amide compound according to any one of items 1 to 3, wherein the group PG is a tert-butoxycarbonyl group (Boc), benzyl group (Bn), benzyloxycarbonyl group (Cbz), benzoyl group (Bz), 2,2,2-trichloroethoxycarbonyl group (Troc), allyloxycarbonyl group (Alloc), 2,4-dinitrophenyl group (2,4-DNP), phthaloyl group (Phth), paramethoxy benzoyl group (PMPCO), cinnamoyl group, toluene sulfonyl group (Ts), 2- or 4-nitrobenzene sulfonyl group (Ns), or 9-fluorenyl methyloxycarbonyl group (Fmoc).

Item 5. The method for producing an amide compound according to any one of items 1 to 4, wherein the amino compound is an amino compound represented by general formula (3) below:

[Chem 3]

(3)

where group $R^a$ and group $R^b$ each independently represent a hydrogen atom, an optionally substituted aliphatic group, an optionally substituted aromatic group, an optionally substituted alicyclic group, or an optionally substituted heterocyclic group, group $R^a$ and group $R^b$ may form, along with a bonding nitrogen atom, a saturated or unsaturated heterocyclic ring, and the heterocyclic ring may have a substituent.

Item 6. The method for producing an amide compound according to any one of items 1 to 4, wherein the amino compound is an amino acid or a salt thereof, or an amino acid ester or a salt thereof.

Item 7. The method for producing an amide compound according to any one of items 1 to 6, wherein the amount of the catalyst used is not more than 20 mol % based on 100 mol % of the aminoester compound.

Item 8. The method for producing an amide compound according to any one of items 1 to 7, wherein the amidation reaction is performed in the presence of a base.

Item 9. The method for producing an amide compound according to any one of items 1 to 8, wherein the amide compound obtained from the amidation reaction is represented by general formula (4) below:

[Chem 4]

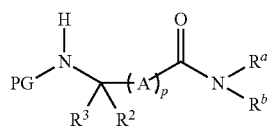

(4)

where group $R^2$ and group $R^3$ are each the same as in general formula (1) above, group $R^a$ and group $R^b$ each independently represent a hydrogen atom, an optionally substituted aliphatic group, an optionally substituted aromatic group, an optionally substituted alicyclic group, or an optionally substituted heterocyclic group, group $R^a$ and group $R^b$ may form, along with a bonding nitrogen atom, a saturated or unsaturated heterocyclic ring. The heterocyclic ring may have a substituent, A represents a linear or branched optionally substituted alkyl group having 1 to 3 carbon atoms, and p is 0 or 1.

Item 10. A method for producing an amide compound, comprising an amidation step wherein, using an amino carboxylic acid compound represented by general formula (11) below and an amino compound in the presence of a catalyst comprising a metal compound, the carboxyl group of the amino carboxylic acid compound is amidated via a metal carboxylate:

[Chem 5]

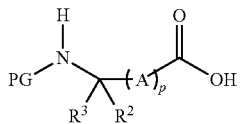

(11)

where group $R^2$ and group $R^3$ each independently represent a hydrogen atom, a halogen atom a hydroxyl group, an optionally substituted aliphatic group, an optionally substituted aromatic group, an optionally substituted alicyclic group, or an optionally substituted heterocyclic group, group PG represents an amino group-protecting group, A represents a linear or branched optionally substituted alkyl group having 1 to 3 carbon atoms, and p is 0 or 1.

Advantageous Effects of the Invention

The present invention provides a novel method for producing an amide compound with high stereochemical selectivity.

DESCRIPTION OF EMBODIMENTS

The method for producing an amide compound of the present invention comprises an amidation step for reacting, in the presence of a catalyst comprising a metal compound, an amino compound with an aminoester compound represented by general formula (1) below to amidate the ester group in the aminoester compound.

[Chem 6]

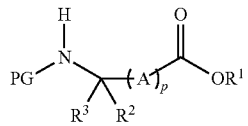

(1)

Additionally, the method for producing an amide compound of the present invention may comprise an amidation step wherein, using an amino carboxylic acid compound represented by the general formula (11) below with an amino compound in the presence of a catalyst comprising a metal compound, and the carboxyl group of the amino carboxylic acid compound is amidated via a metal carboxylate. Basically, this method for producing an amide compound performs amidation by using an amino carboxylic acid compound as a starting material, generating a metal carboxylate in the system by converting the carboxyl group of the amino carboxylic acid compound with a metal reagent, and thereby reacting the amino carboxylic acid compound with an amino compound. As described hereinafter, in this method, amidation can be made to occur by reacting an amino carboxylic acid and an amino compound via a metal carboxylate.

[Chem 7]

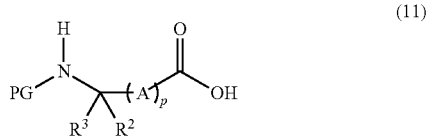

(11)

The following is an explanation of the method for producing an amide compound of the present invention. As described hereinafter, in the present invention, the amide compound of the present invention is produced by reacting the ester group (or the metal carboxylate generated from the carboxyl group of an amino carboxylic acid compound represented by the general formula (11) above) of an aminoester compound represented by the general formula (1) above with an amino group of the amino compound to form an amide bond.

In the present specification, the term "to" used to indicate a numerical range indicates that the value is not less than the left side value and not greater than the right side value, such that the numerical range X to Y indicates values from X to Y inclusive.

In the aminoester compound (hereinafter occasionally referred to as aminoester compound (1)) represented by the general formula (1) above, group $R^1$ represents an optionally substituted aliphatic group, an optionally substituted aromatic group, an optionally substituted alicyclic group, or an optionally substituted heterocyclic group.

Further, groups $R^2$ and $R^3$ shown in general formulas (1) and (11) above each independently represent a hydrogen atom, a halogen atom, a hydroxyl group, an optionally substituted aliphatic group, an optionally substituted aromatic group, an optionally substituted alicyclic group, or an optionally substituted heterocyclic group.

The substituents of groups $R^1$, $R^2$, and $R^3$ (substituent groups of the aliphatic groups, alicyclic groups, and heterocyclic groups) are not particularly limited as long as the amidation step of the present invention proceeds, and may each independently be, for example, an alkyl group (for example, a linear or branched alkyl group having 1 to 10 carbon atoms, an alkenyl group (for example, a linear or branched alkenyl group having 1 to 10 carbon atoms), an alkynyl group (for example, a linear or branched alkynyl group having 1 to 10 carbon atoms), an alkoxy group (for example, a linear or branched alkenyl group having 1 to 10 carbon atoms), a hydroxyl group, a halogen atom, a nitro group, a thiol group, or a cyano group. Additionally, when the aliphatic groups, aromatic groups, alicyclic groups, and heterocyclic groups for groups $R^1$, $R^2$, and $R^3$ have substituents, the numbers of substituents are not particularly limited, but may each independently be, for example, 1 to 10, 1 to 5, 1 to 3, 1 or 2, or 1. When there are multiple substituents, the substituents can be of a single type or of two or more types. Furthermore, aliphatic groups and aromatic groups may each include a hetero atom. The aliphatic groups, alicyclic groups, and heterocyclic groups can each be saturated or unsaturated.

Group $R^1$ is preferably an optionally substituted aliphatic group having 1 to 20 carbon atoms, an optionally substituted aromatic group having 4 to 20 carbon atoms, an optionally substituted alicyclic group having 3 to 20 carbon atoms, an optionally substituted heterocyclic group having 2 to 20 carbon atoms, or more preferably, an optionally substituted aliphatic group having 1 to 10 carbon atoms, an optionally substituted aromatic group having 4 to 10 carbon atoms, an optionally substituted alicyclic group having 3 to 10 carbon atoms, or an optionally substituted heterocyclic group having 2 to 10 carbon atoms. Specific examples of group $R^1$ include linear or branched alkyl groups each having 1 to 10 carbon atoms, such as a methyl group, an ethyl group, a propyl group, an isopropyl group, a butyl group, a sec-butyl group, a tert-butyl group, a propargyl group; phenylalkyl groups each having a linear or branched alkyl group having 1 to 10 carbon atoms, such as a phenyl group, or a benzyl group; and linear or branched alkenyl groups each having 1 to 10 carbon atoms such as allyl groups. Additionally, the substituents for group $R^1$ are as described above.

Additionally, groups $R^2$ and $R^3$ bonded to a carbon atom in the general formulas (1) and (11) are, preferably, each independently a hydrogen atom, a halogen atom, a hydroxyl group, an optionally substituted aliphatic group having 1 to 20 carbon atoms, an optionally substituted aromatic group having 4 to 20 carbon atoms, an optionally substituted alicyclic group having 3 to 20 carbon atoms, or an optionally substituted heterocyclic group having 2 to 20 carbon atoms; or more preferably, a hydrogen atom, a halogen atom, a hydroxyl group, an optionally substituted aliphatic group having 1 to 10 carbon atoms, an optionally substituted aromatic group having 4 to 10 carbon atoms, an optionally substituted alicyclic group having 3 to 10 carbon atoms, or an optionally substituted heterocyclic group having 2 to 10 carbon atoms. Specific examples of groups $R^2$ and $R^3$ each independently include a hydrogen atom, a hydroxyl group, a nitro group, a thiol group, a cyano group, a phenyl group; halogen atoms, such as a fluorine atom, a chlorine atom, a bromine atom, and an iodine atom; linear or branched alkyl groups each having 1 to 10 carbon atoms, such as a methyl group, an ethyl group, a propyl group, an isopropyl group, or a butyl group; linear or branched alkenyl groups each having 1 to 10 carbon atoms, such as an ethylene group, a propylene group, or a butylene group; an alkynyl group having 1 to 10 carbon atoms such as a propargyl group; and linear or branched alkoxy groups each having 1 to 10 carbon atoms, such as a methoxy group, an ethoxy group, a propoxy group, a butoxy group, a sec-butoxy group, or a tert-butoxy group.

A represents a linear or branched optionally substituted alkylene group having 1 to 3 carbon atoms. Specifically, A is a methylene group, an ethylene group, a propylene group, or the like. Additionally, p is 0 or 1. The substituents can be any of the substituents indicated above for $R^1$, $R^2$, and $R^3$.

Group PG is an amino group-protecting group. The amino group-protecting group is not particularly limited, as long as it can prevent the amino group from reacting in the method for producing an amide compound, and backward conversion into the amino group due to deprotection after the reaction has finished is possible. A wide variety of amino group-protecting groups are publicly known. The number of carbon atoms in a protecting group is usually about 1 to 20 or preferably about 3 to 15.

In the present invention, group PG may comprise a hydroxyl group or not comprise a hydroxyl group. Additionally, groups $R^2$ and $R^3$ may each independently comprise a hydroxyl group or not comprise a hydroxyl group. In the general formula (1) above, the position adjacent the ester group is α-position (carbon atom), the next position is β-position (nitrogen atom), but when the next position after β is defined as the γ-position, and the position after that is defined as the δ-position, for the case when at least one of groups PG, $R^2$, and $R^3$ comprises a hydroxyl group, a hydroxy group may bond to an atom in a position other than the α-position, β-position, γ-position, and δ-position, without any hydroxy group bonding to the atom in the α-position, β-position, γ-position, or δ-position. Basically, the aminoester compound represented by general formula (1) may not correspond to any of an α-hydroxy ester compound, β-hydroxy ester compound, γ-hydroxy ester compound, and δ-hydroxy ester compound. Furthermore, in the case that the aminoester compound represented by general formula (1) is one of an α-hydroxy ester compound, β-hydroxy ester compound, γ-hydroxy ester compound, and δ-hydroxy ester compound, the amino compound reacts with the carbonyl carbon with high selectivity because the metal catalyst is coordinated with the hydroxy group bonded to the α-position, β-position, γ-position, or δ-position and the ester group. The same applies to the general formula (11) above.

Typical examples of this type of protecting group include substituted or non-substituted acyl groups, carbamates, amides, aryl groups, aralkyl groups, and alkenyl groups. As for the nomenclature of the protecting group, there are some names referring to groups bonded to the N atom of the amino group, and some names referring to groups including an N atom. The following includes both types of name: benzoyl group (Bz), orthomethoxybenzoyl group, 2,6-dimethoxybenzoyl group, paramethoxybenzoyl group (PMPCO), 2,2, 2-trichloroethoxycarbonyl group (Troc), allyloxycarbonyl group (Alloc), cinnamoyl group, phthaloyl group (Phth), and 9-fluorenylmethyloxycarbonyl group (Fmoc). Specific examples of a carbamate include tert-butoxycarbonyl group (Boc), benzyloxycarbonyl group (Cbz), methyl carbamate, ethyl carbamate, 2-trimethylsilylethyl carbamate, 2-phenylethyl carbamate, 1-(1-adamantyl)-1-methylethyl carbamate, 1-(3,5-di-t-butylphenyl)-1-methylethyl carbamate, vinyl carbamate, allyl carbamate, N-hydroxypiperidinyl carbamate, p-methoxybenzyl carbamate, p-nitrobenzyl carbamate, [2-(1,3-dithianyl) methyl carbamate, m-nitrophenyl carbamate, 3,5-dimethoxybenzyl carbamate, and o-nitrobenzyl carbamate. Specific examples of an amide include acetamide, o-(benzoyloxymethyl) benzamide, 2-[(t-butyldiphenylsiloxane) methyl] benzamide, 2-toluenesulfonamide, 4-toluenesulfonamide, 2-nitrobenzenesulfonamide, 4-nitrobenzenesulfonamide, tert-butylsulfinylamide, 4-toluenesulfonamide, 2-(trimethylsilyl)ethanesulfonamide, benzylsulfonamide. The acyl group may be derived from an aromatic or heterocyclic carboxylic acid or sulfonic acid. Specific examples of an aryl group include 2,4-dinitrophenyl group (2,4-DNP). Specific examples of an aralkyl group include a benzyl group (Bn) and a phenethyl group. Specific examples of an alkenyl group include a vinyl group, an allyl group, and a hexenyl group.

Considering deprotection methods, the protecting group may be a protecting group which can be deprotected by at least one method, such as deprotection by hydrogenation, deprotection by weak acid, deprotection by fluorine ions, deprotection by one-electron deoxidizer, deprotection by hydrazine, or deprotection by oxygen.

Specific examples of preferable protecting groups include a tert-butoxycarbonyl group (Boc), benzyl group (Bn), benzyloxycarbonyl group (Cbz), benzoyl group (Bz), 2,2,2-trichloroethoxycarbonyl group (Troc), allyloxycarbonyl group (Alloc), 2,4-dinitrophenyl group (2,4-DNP), phthaloyl group (Phth), paramethoxybenzoyl group (PMPCO), cinnamoyl group, toluenesulfonyl group (Ts), 2- or 4-nitrobenzenesulfonyl group (Ns), and 9-fluorenyl methyloxycarbonyl group (Fmoc).

In the present invention, the amino compound is not particularly limited provided it reacts with an aminoester compound (1) or an amino carboxylic acid compound (11) to form an amide group. For example, primary amines or secondary amines are preferable because they have high reactivity with ester groups.

Preferable amino compounds, if represented as a general formula, can be represented by, for example, general formula (3) below.

[Chem 8]

(3)

In the amino compound represented by the general formula (3) (hereinafter occasionally referred to as amino compound (3)), group $R^a$ and group $R^b$ each independently represent a hydrogen atom, an optionally substituted aliphatic group, an optionally substituted aromatic group, an optionally substituted alicyclic group, or an optionally substituted heterocyclic group. Additionally, group $R^a$ and group $R^b$ may form, along with a bonding nitrogen atom, a saturated or unsaturated heterocyclic ring. The heterocyclic ring may have a substituent.

The substituent of the heterocyclic ring formed of group $R^a$ and group $R^b$ along with the bonding nitrogen is not particularly limited as long as the heterocyclic ring reacts with either an aminoester compound (1) or an amino carboxylic acid compound (11) to form an amide group, and the substituents can each independently be, for example, an alkyl group (for example, a linear or branched alkyl group having 1 to 10 carbon atoms), an alkenyl group (for example, a linear or branched alkenyl group having 1 to 10 carbon atoms), an alkynyl group (for example, a linear or branched alkynyl group having 1 to 10 carbon atoms), an alkoxy group (for example, a linear or branched alkoxy group having 1 to 10 carbon atoms), a hydroxyl group, a halogen atom, a nitro group, a thiol group, a cyano group, a linear or branched alkylthio group having 1 to 10 carbon atoms, an optionally substituted amino group, and an optionally substituted amide group, an optionally substituted guadinino group, a —$COOR^1$ group ($R^1$ is the same as above), an optionally substituted aryl group, an optionally substituted heterocyclic group. The substituents for the optionally substituted amino group, the optionally substituted amide group, the optionally substituted guadinino group, the optionally substituted aryl group, and the optionally substituted heterocyclic group are the same as defined for the group $R^a$ and group $R^b$ above. The aryl group can be a phenyl group. The heterocyclic group can be an indolyl group or an imidazolyl group. If the aliphatic groups, aromatic groups, alicyclic groups, or heterocyclic groups in group $R^1$, group $R^2$ and the ring structure formed by linking therebetween have substituents, the numbers of substituents are not particularly limited, and can each independently be 1 to 10, 1 to 5, 1 to 3, 1 or 2, or 1. If there are multiple substituents, the substituents can be of a single type, or of two or more types. Furthermore, the aliphatic group and the aromatic group can each comprise a heteroatom. Additionally, the aliphatic group, alicyclic group, and heterocyclic group each can be saturated or can be unsaturated.

Group $R^a$ and group $R^b$ of amino compound (3) can each independently preferably be a hydrogen atom, an optionally substituted aliphatic group having 1 to 20 carbon atoms, an optionally substituted aromatic group having 4 to 20 carbon atoms, an optionally substituted alicyclic group having 3 to 20 carbon atoms, an optionally substituted heterocyclic group having 2 to 20 carbon atoms, or more preferably, a hydrogen atom, an optionally substituted aliphatic group having 1 to 10 carbon atoms, an optionally substituted aromatic group having 4 to 10 carbon atoms, an optionally substituted alicyclic group having 3 to 10 carbon atoms, or an optionally substituted heterocyclic group having 2 to 10 carbon atoms. However, it is not preferable for both group $R^a$ and group $R^b$ to be hydrogen atoms (i.e., the case when the amino compound is ammonia), because the boiling point of the compound is low. The substituents of group $R^a$ and group $R^b$ are each as described previously.

Specific examples of the saturated or unsaturated heterocyclic ring formed of $R^a$ and $R^b$ with the boding nitrogen atom include 5 to 6-membered saturated or unsaturated heterocyclic groups such as pyrrolinyl, pyrrolyl, 2,3-dihydro-1H-pyrrolyl, piperidinyl, piperazinyl, homopiperazinyl, morpholino, thiomorpholino, 1,2,4,6-tetrahydropyridyl, hexahydropyrimidyl, hexahydropyridazyl, 1,2,4,6-tetrahydropyridyl, 1,2,4,6-tetrahydropyridazyl, 3,4-dihydropyridyl, imidazolyl, 4,5-dihydro-1H-imidazolyl, 2,3-dihydro-1H-imidazolyl, pyrazolyl, 4,5-dihydro-1H-pyrazolyl, 2,3-dihydro-1H-pyrazolyl, oxazolyl, 4,5-dihydro-1,3-oxazolyl, 2,3-dihydro-1,3-oxazolyl, 2,5-dihydro-1,3-oxazolyl, thiazolyl, 4,5-dihydro-1,3-thiazolyl, 2,3-dihydro-1,3-thiazolyl, and 2,5-dihydro-1,3-thiazolyl.

In the present invention, the amino compound is preferably an amino acid or a salt thereof, or an amino acid ester or a salt thereof. Since the method for producing an amide compound of the present invention can be used to produce an amide compound with high stereochemical selectivity, peptides can be synthesized with high stereochemical selectivity by reacting an aminoester compound (1) or an amino carboxylic acid compound (11) with an amino acid having an asymmetric center or a salt thereof or an amino acid ester having an asymmetric center or a salt thereof. The amino compound (3) above encompasses amino acids and salts thereof and amino acid esters and salts thereof.

The amino acid is not particularly limited, and can be a publicly known amino acid such as an oligomer (usually from a dimer to a decamer) of amino acids containing at least one of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Examples of the ester of the amino acid include esters in which the carboxylic acid of the amino acid is esterified with a linear or branched alkyl group having 1 to 10 carbon atoms, a linear or branched alkenyl group having 1 to 10 carbon atoms such as a propargyl group, or an aryl group. Additionally, the amino acid salt or amino acid ester salt can be any of hydrochlorides, sulfates, oxalated, and phosphates of these amino acids and amino acid esters.

In the method for producing an amide compound of the present invention, for example, the reaction of the aminoester compound (1) with the amino compound (3) can be represented by the following reaction formula. In the present invention, an amide compound (4) can be produced well by the reaction below.

[Chem 9]

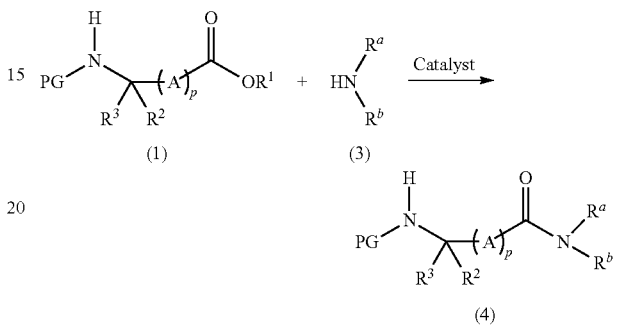

In the method for producing an amide compound of the present invention, for example, the reaction of the amino carboxylic acid compound (11) and the amino compound (3) can be represented by the following reaction formula. In the present invention, an amide compound can be produced well by the reaction below as well. In the reaction below, the amide compound (4) is generated using a metal catalyst to make the carboxyl group of the amino carboxylic acid compound (11) into a metal carboxylate which can react with the amino compound (3).

[Chem 10]

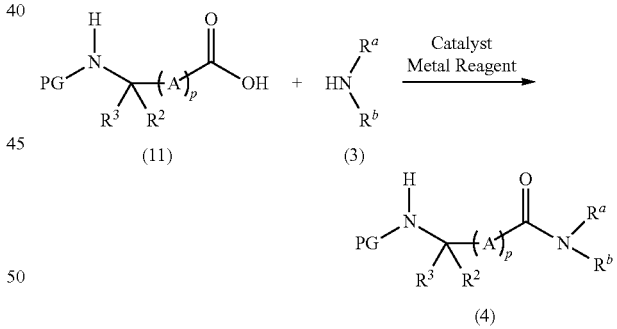

The molar ratio of aminoester compound (1) to amino compound in the method for producing an amide compound of the present invention is not particularly limited, but the amino compound can be used in an amount of about 0.1 mol to 10 mol, preferably about 0.1 mol to 5 mol, about 1 mol to 10 mol, or more preferably about 1 mol to 5 mol relative to 1 mol of aminoester compound (1). Additionally, the molar ratio of amino carboxylic acid compound (11) to amino compound in the method for producing an amide compound of the present invention is likewise not particularly limited, but the amino compound can be about 0.1 mol to 10 mol, preferably about 0.1 mol to 5 mol, about 1 mol to 10 mol, or more preferably about 1 mol to 5 mol relative to 1 mol of amino carboxylic acid compound (11).

However, regarding the amide compound (for example, a compound represented by general formula (4) above) obtained after the amidation step, when an amino compound is produced via a deprotection step for deprotecting group PG in the β-position derived from either the aminoester compound represented by general formula (1) or the amino carboxylic acid compound represented by general formula (11) to obtain a converted amino group, and the amino compound is then reacted with the aminoester compound (1) or the amino carboxylic acid compound represented by general formula (11) to produce a dipeptide, or when a plurality of peptide bonds are formed by repeating the method above to form an oligopeptide, the use of the aminoester compound or amino carboxylic acid compound in excess in comparison to the amino compound used in the reaction is advantageous from the perspective of cost. Essentially, in the present invention, aminoester compound (1) and amino carboxylic acid compound (11) can be used as amino acid units that sequentially form bonds with amino compounds, and aminoester compound (1) and amino carboxylic acid compound (11) derived from amino acid can be prepared relatively inexpensively.

In the method for producing an amide compound of the present invention, the metal compound used as a catalyst is not particularly limited, provided it encourages the amidation step in which the ester group of the aminoester compound is amidated (or the amidation step in which the metal carboxylate generated from the carboxyl group of the amino carboxylic acid compound is amidated). The metal compound is preferably a metal compound that can function as a Lewis acid.

The metal constituting the metal compound can be any of the metals from group 2 to group 5 of the periodic table of the elements. Specific examples of the metal constituting the metal compound include boron, magnesium, aluminum, gallium, indium, silicon, calcium, lead, bismuth, mercury, transition metals, and lanthanide elements. Specific examples of the transition metals include scandium, titanium, vanadium, chromium, manganese, iron, cobalt, nickel, copper, zinc, yttrium, zirconium, niobium, molybdenum, technetium, ruthenium, rhodium, palladium, tin, silver, cadmium, hafnium, tantalum, tungsten, rhenium, osmium, iridium, platinum, gold, and thallium. Specific examples of lanthanoid elements include lanthanum, cerium, neodymium, samarium, europium, gadolinium, holmium, erbium, thulium, and ytterbium. Of these, tantalum, boron, vanadium, tungsten, hafnium, niobium, neodymium, iron, lead, cobalt, copper, silver, palladium, tin, and thallium are particularly preferable from the perspective of excellent reaction promotion and producing amide compounds with high stereochemical selectivity.

The catalyst may comprise one of the metal compounds above, or may comprise two or more of the metal compounds above.

In particular, if the aminoester compound (1) is an oxime compound (11), from the perspective of excellent reaction promotion and producing an amide compound with high stereochemical selectivity, it is preferable for the catalyst to comprise at least one metal compound selected from a tantalum compound, a niobium compound, a vanadium compound, a tungsten compound, a hafnium compound, a neodymium compound, an iron compound, a lead compound, a cobalt compound, and a copper compound, and more preferable for the catalyst to comprise at least one of a tantalum compound and a niobium compound.

The ligand of the metal compound can be appropriately selected in accordance with the type of metal. Specific examples of the ligand include linear or branched alkoxy groups each having 1 to 10 carbon atoms, such as a methoxy group, an ethoxy group, a propoxy group, and a butoxy group; halogen atoms, such as a fluorine atom, a chlorine atom, a bromine atom, and an iodine atom; allyloxy groups each having about 1 to 10 carbon atoms, an acetylacetonato group (acac), an acetoxy group (AcO), a trifluoromethanesulfonate group (TfO), linear or branched alkyl groups each having 1 to 10 carbon atoms, a phenyl group, an oxygen atom, a sulfur atom, an —SR group, an —NRR' group, and a cyclopentadienyl (Cp) group. The R of the —SR group can be a linear or branched alkyl, alkenyl, or aryl group having 1 to 10 carbon atoms. The R and R' groups of the —NRR' group can each independently be a hydrogen atom, or a linear or branched alkyl, alkenyl, or aryl group having about 1 to 10 carbon atoms.

For example, specific examples of the preferable tantalum compound include tantalum compounds represented by $TaX^1_5$ (wherein the five $X^1$ groups are each independently any of the ligands indicated above; normally, the five $X^1$ groups are the same group). The alkoxy group of $X^1$ is preferably a linear or branched alkoxy group having 1 to 10 carbon atoms, more preferably a linear or branched alkoxy group having 1 to 5 carbon atoms, or even more preferably a linear or branched alkoxy group having 1 to 3 carbon atoms. The allyloxy group is preferably an allyloxy group having 1 to 20 carbon atoms, more preferably an allyloxy group having 1 to 15 carbon atoms, or even more preferably an allyloxy group having 1 to 10 carbon atoms. The halogen atom is preferably a chlorine atom or a bromine atom. Of these, tantalum alkoxy compounds (for example, $X^1$ is an alkoxy group), such as $Ta(OMe)_5$, $Ta(OEth)_5$, $TA(OBu)_5$, $Ta(NMe_2)_5$, $Ta(acac)(OEth)_4$, $TaCl_5$, $TaCl_4(THF)$, and $TaBr_5$, are preferable.

Specific examples of the preferable niobium compound include niobium compounds represented by $NbX^2_5$ (wherein the five $X^2$ groups are each independently any of the ligands indicated above; normally, the five $X^2$ groups are the same group). The alkoxy group of $X^2$ is preferably a linear or branched alkoxy group having 1 to 10 carbon atoms, more preferably a linear or branched alkoxy group having 1 to 5 carbon atoms, or even more preferably a linear or branched alkoxy group having 1 to 3 carbon atoms. The allyloxy group is preferably an allyloxy group having 1 to 20 carbon atoms, more preferably an allyloxy group having 1 to 15 carbon atoms, or even more preferably an allyloxy group having 1 to 10 carbon atoms. The halogen atom is preferably a chlorine atom or a bromine atom. Of these, niobium alkoxy compounds (for example, $X^2$ is an alkoxy group), such as $NbCl_4(THF)$, $NbCl_5$, and $Nb(OEt)_5$, are preferable.

Specific examples of the preferable hafnium compound include hafnium compounds represented by $HfX^3_4$ (wherein the four $X^3$ groups are each independently any of the ligands indicated above; normally, the four $X^3$ groups are the same group). The alkoxy group of $X^3$ is preferably a linear or branched alkoxy group having 1 to 10 carbon atoms, more preferably a linear or branched alkoxy group having 1 to 5 carbon atoms, or even more preferably a linear or branched alkoxy group having 1 to 4 carbon atoms. The allyloxy group is preferably an allyloxy group having 1 to 20 carbon atoms, more preferably an allyloxy group having 1 to 15 carbon atoms, or even more preferably an allyloxy group having 1 to 10 carbon atoms. The halogen atom is preferably a chlorine atom or a bromine atom. Of these, niobium alkoxy compounds (for example, $X^2$ is an alkoxy group), such as $HfCp_2Cl_2$, are preferable.

Specific examples of the preferable copper compound include copper compounds represented by $CuX^4_2$ (wherein the two $X^4$ groups are each independently any of the ligands indicated above; normally, the two $X^4$ groups are the same group) and $CuX^5$ (wherein $X^5$ is a ligand indicated above). Of these, for example, $Cu(OAc)_2$ is preferable.

Specific examples of the preferable palladium compound include the palladium compounds represented by $PdX^6_2$ (wherein the two $X^6$ are each independently any of the ligands indicated above; normally, the two $X^6$ groups are the same group). Of these, for example, $Pd(OAc)_2$ is preferable.

The catalyst may be carried by a carrier. The carrier which carries the catalyst is not particularly limited, and can be a publicly known carrier. Additionally, the method for loading the catalyst on the carrier can be a publicly known method.

The amount of catalyst to be used is not particularly limited, but the amount of catalyst is preferably not greater than 30 mol %, or more preferably about 0.1 mol % to 20 mol %, based on 100 mol % of the aminoester compound (1) (or 100 mol % of the amino carboxylic acid compound (11)).

The metal reagent used to make the carboxyl group of the amino carboxylic acid compound into a metal carboxylate for reacting with the amino compound is not particularly limited, but is preferably a metal reagent capable of converting the carboxyl group to a metal carboxylate upon mixing with an amino carboxylic acid compound. The metal reagent can be a publicly known metal reagent, such as N-trimethylsilylimidazole, arylboric acid ($ArB(OH)_2$), zirconium chloride ($ZrCl_4$), or zirconocene dichloride ($Cp_2ZrCl_2$).

The amount of metal reagent to be used is not particularly limited, but the amount of metal reagent can be, for example, about 100 to 300 parts by mass, or preferably about 150 to 220 parts by mass relative to 100 parts by mass of the amino carboxylic acid compound (11).

The method for producing an amide compound of the present invention may be performed in the presence of a base, from the perspective of increasing reaction efficacy. The base is not particularly limited, but can be, for example, an amine having 1 to 3 linear or branched alkyl groups each having 1 to 10 carbon atoms, such as triethylamine ($Et_3N$), diisopropylamine (i-$Pr_2NH$), or diisopropylethylamine (i-$Pr_2EtN$).

The amount of base to be used is not particularly limited, but is preferably about 20 to 120 mol %, or more preferably about 50 to 100 mol % based on 100 mol % of the aminoester compound (1) (or 100 mol % of the amino carboxylic acid compound (11)).

The method for producing an amide compound of the present invention may be performed in an organic solvent, from the perspective of increasing reaction efficacy. The organic solvent is not particularly limited, and can be, for example, an aromatic hydrocarbon, such as toluene or xylene, pentane, an ether such as petroleum ether, 1-methyltetrahydofuran (1-MeTHF), diisopropyl ether (i-$Pr_2O$), diethyl ether ($Et_2O$), or cyclopentylmethyl ether (CPME), an ester, such as ethyl acetate (AcOEt), or an organic acid, such as acetic acid. These organic solvents can be used solely or in combination of two or more. The concentrations of the aminoester compound (1) and amino carboxylic acid compound (11) in the reaction are not particularly limited, but are preferably 2 vol % to 70 vol % from the perspective of enhancing reaction efficacy.

The reaction temperature in the method for producing an amide compound of the present invention is not particularly limited, but is preferably about 0° C. to 150° C. from the perspective of enhancing reaction efficacy. The reaction time is not particularly limited, but can be, for example, about 10 minutes to 80 hours.

The method for producing an amide compound of the present invention can be carried out under atmospheric pressure, under low pressure, or under high pressure. From the perspective of carrying out the reaction simply, the reaction is preferably carried out under atmospheric pressure. The production of the amide compound is preferably carried out in an atmosphere of inert gas, such as nitrogen.

The method for producing an amide compound of the present invention may be carried out in the presence of ligands. The ligands are not particularly limited, and can be, for example, 2,2'-bipyridine, 8-hydroxyquinoline, [2,2'-bisquinoline]-8,8'-diol, or 2,2':6,2":6",2'''-quarter pyridine. Depending on the position of the heteroatom in the ligand, the coordinating form of the metal of the metal compound used as the catalyst can differ, and amidation reactions can proceed at a variety of distances.

The amount of ligand is not particularly limited, but is preferably not more than 20 mol %, and more preferably about 0.1 mol % to 10 mol %, based on 100 mol % of the aminoester compound (1) (or 100 mol % of the amino carboxylic acid (11)).

Thus, amide compounds are suitably generated by the production method of the present invention.

The amide compound generated according to the method for producing an amide compound of the present invention can be purified according to a standard method. The isolated amide compound can be used in a variety of applications.

The method for producing an amide compound of the present invention may further comprise a deprotection step wherein after the amidation step, in the obtained amide compound, protecting group PG derived from the aminoester compound represented by general formula (1) or the amino carboxylic acid compound represented by the general formula (11) above is deprotected to obtain a converted amino group. An amino group can be introduced into the amide compound by this deprotection step.

Additionally, using the amide compound having an amino group introduced therein via the deprotection-reduction step (i.e., the amide compound having an amino group), an amidation step for amidating the ester group of an aminoester compound (1) can be performed by reacting the aminoester compound (1) with the amide compound comprising an amino group in the presence of a catalyst comprising the metal compound. Similarly, using the amide compound having an amino group introduced therein via the deprotection-reduction step (i.e., the amide compound having an amino group), an amidation step for amidating a metal carboxylate can be performed by reacting the amino carboxylic acid compound (11) with the amide compound comprising an amino group in the presence of a catalyst comprising the metal compound.

Thus, in the present invention, the structure of the aminoester compound (1) or the amino carboxylic acid compound (11) subjected repeatedly to addition can be selected from various structures, whereby an amide compound comprising desired amino acid units linked via peptide bonding can be synthesized, and a desired oligopeptide can be produced with high stereochemical selectivity.

A wide variety methods in accordance with the type of protecting group are known as the method for introducing a protecting group to an amino group and the method for deprotecting the protecting group to regain the amino group. Thus, the method of deprotection is not particularly limited, and can be a method of deprotection in accordance with the protecting group used. Methods of deprotection include, as indicated previously, deprotection by hydrogenation, deprotection by weak acid, deprotection by fluorine ions, deprotection by one-electron deoxidizer, deprotection by hydrazine, and deprotection by oxygen.

Examples of the deprotection by hydrogenation include (a) a method of deprotection by using a metal catalyst such as palladium, palladium-carbon, palladium hydroxide, or palladium hydroxide-carbon in presence of hydrogen gas to reduce and remove the protecting group, and (b) a method of deprotection by using a hydrogenation reducing agent such as sodium borohydride, lithium aluminum hydride, lithium borohydride, or diborane in the presence of a metal catalyst such as palladium, palladium-carbon, palladium hydroxide, or palladium hydroxide-carbon to reduce and remove the protecting group.

In the present invention, the amino compound represented by the general formula (5) below can be produced by deprotection of protecting group PG of the amide compound represented by the general formula (4) below according to the reaction formula below.

[Chem 11]

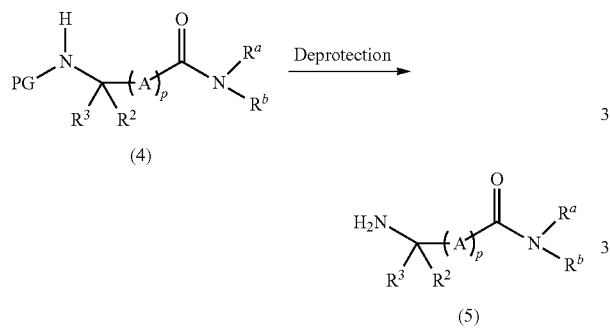

(4)

(5)

In the general formula (5), groups $R^2$, $R^3$, $R^a$, and $R^b$ are the same as in the general formula (4).

The method for removing protecting group PG can be any of the various deprotection methods indicated above, and is preferably deprotection by hydrogenation. Regarding the conditions for deprotection by hydrogenation, the suitable conditions are publicly known and can be appropriately determined in accordance with the type of protecting group. For example, the catalyst used in deprotection by hydrogenation can be any of the catalysts indicated above. The amount of catalyst is not particularly limited, but is preferably about 1 to 20 mol % based on 100 mol % of the amide compound represented by the general formula (4). Additionally, the solvent can be an alcohol such as methanol, ethanol, or 2-propanol, an ester such as ethyl acetate, an ether such as tetrahydrofuran, or 1,4-dioxane. The reaction temperature can normally be about 0 to 100° C. The reaction time can normally be about 1 to 48 hours. The pressure of the hydrogen gas can normally be about 1 to 10 atm.

EXAMPLES

The present invention will be specifically described by way of the Examples and Comparative Examples, but the present invention is not limited thereto. In the Examples below, "cat" means "catalyst" and "r.t." means "room temperature" (about 23° C.). Unless stated otherwise, the yields are values obtained via GC analysis using octane as an internal standard or via isolation using a chromatographer. The diastereoselectivity is a value obtained by $^1$H-NMR analysis. Identification of generated products was performed using $^1$H-NMR analysis and liquid chromatography-mass spectrometry (LC-MS).

Example 1

As shown in the formula below, the amide compound 2 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester hydrochloride 1 (Bn-L-Ala-OMe) comprising an amino group protected by a benzyl group (Bn) (1.5 equivalents) in an atmosphere of nitrogen gas in the presence of triethylamine ($Et_3N$) (2.5 equivalents) as a base and a catalyst (10 mol %) at 60° C. The yields are shown in Table 1.

[Chem 12]

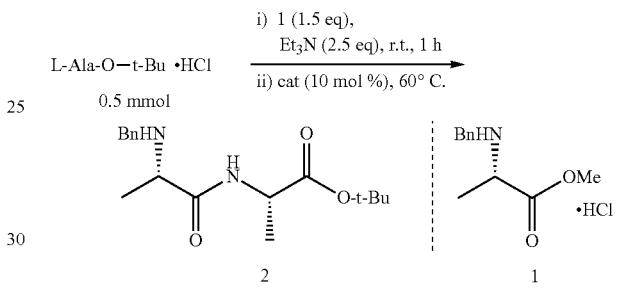

TABLE 1

| Entry | cat | Time (h) | yield of 2$^a$ (%) |
|---|---|---|---|
| 1 | Ta(OEt)$_5$ | 48 | 53 |
| 2 | Nb(OEt)$_5$ | 24 | 15 |
| 3 | Ta(OEt)$_5$ | 24 | 27 |

In Table 1, the yields are values obtained via GC analysis using octane as an internal standard (Note a).

Example 2

As shown in the formula below, the amide compound 2 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester hydrochloride 1 (Bn-L-Ala-OMe) comprising an amino group protected by a benzyl group (Bn) (1.5 equivalents) in an atmosphere of nitrogen gas in the presence of triethylamine ($Et_3N$) as a base in a properly set amount and Ta(OEt)$_5$ (10 mol %) as a catalyst at 60° C. for 24 hours. The yields are shown in Table 2.

[Chem 13]

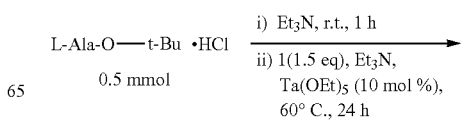

-continued

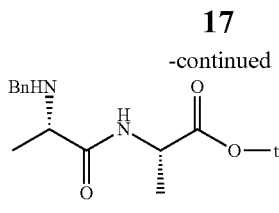 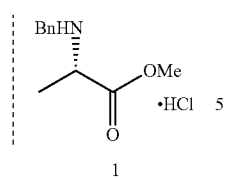

2    1

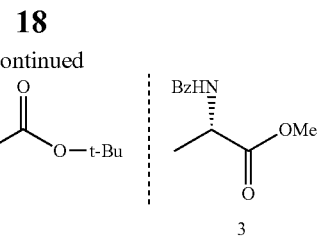 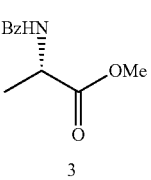

4    3

TABLE 2

| Entry | Et$_3$N (eq) | yield of 2[a] (%) |
|---|---|---|
| 1 | i) 2.5, ii) 0 | 29 |
| 2 | i) 1.0, ii) 1.5 | 21 |

In Table 2, the yields are isolated yields (Note a).

Example 3

As shown in the formula below, the amide compound 4 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester 3 (Bz-L-Ala-OMe) comprising an amino group protected by a benzoyl group (Bz) (in the amount indicated in Table 3) in an atmosphere of nitrogen gas in the presence of triethylamine (Et$_3$N) (1.0 equivalent) as a base and the catalyst (10 mol %) indicated in Table 3 under the temperature and reaction time conditions indicated in Table 3. The yields are shown in Table 3.

TABLE 3

| Entry | Cat | 3 (eq) | temp (° C.) | time (h) | yield of 4[a] (%) |
|---|---|---|---|---|---|
| 1 | Ta(OMe)$_5$ | 1.5 | 50 | 24 | 65 |
| 2 | Ta(OEt)$_5$ | 1.5 | 50 | 24 | 62 |
| 3 | Ta(OBu)$_5$ | 1.5 | 50 | 24 | 42 |
| 4 | Nb(OEt)$_5$ | 1.5 | 50 | 24 | 12 |
| 5 | Cp$_2$HfCl$_2$ | 1.5 | 50 | 24 | 24 |
| 6 | Ta(OEt)$_5$ | 1.3 | 50 | 24 | 51 |
| 7 | Ta(OEt)$_5$ | 1.7 | 50 | 24 | 58 |
| 8 | Ta(OEt)$_5$ | 1.5 | 50 | 48 | 70 |
| 9 | Ta(OMe)$_5$ | 1.5 | 60 | 24 | 82 |
| 10 | Ta(OEt)$_5$ | 1.5 | 60 | 24 | 70 |
| 11 | Ta(OEt)$_5$ | 1.5 | 60 | 48 | 81 |
| 12 | Ta(OEt)$_5$ | 1.5 | 70 | 48 | 52 |
| 13 | Ta(OEt)$_5$ | 1.5 | 80 | 24 | 43 |

In Table 3, the yields are isolated yields (Note a).

Example 4

As shown in the formula below, the amide compound (dipeptide precursor) represented by the formula below was synthesized by reacting L-alanine t-butyl ester hydrochloride (L-Ala-Ot-Bu-HCl, 0.5 mmol) as an amino compound with L-alanine methyl ester 5 (PMPCO-L-Ala-OMe) comprising an amino group protected by a paramethoxybenzoyl group (PMPCO) (1.5 equivalents) in an atmosphere of nitrogen gas in the presence of triethylamine (Et$_3$N) (1.0 equivalent) as a base and the catalyst (10 mol %) indicated in Table 4 under the temperature and reaction time conditions indicated in Table 4. The yields are shown in Table 4.

[Chem 14]

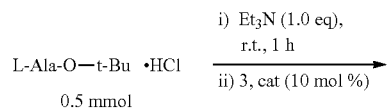

[Chem 15]

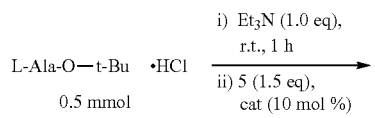

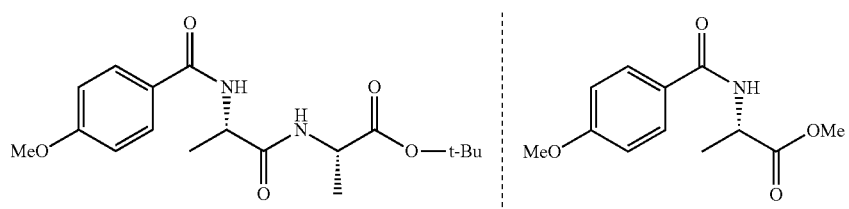

6    5

TABLE 4

| Entry | Cat | temp (° C.) | time (h) | yield of 6[a] (%) |
|---|---|---|---|---|
| 1 | Ta(OMe)$_5$ | 60 | 24 | 48 |
| 2 | Ta(OMe)$_5$ | 60 | 48 | 75 |
| 3 | Ta(OMe)$_5$ | 70 | 48 | 57 |
| 4 | Ta(OEt)$_5$ | 60 | 24 | 14 |
| 5 | Ta(OEt)$_5$ | 60 | 48 | 17 |

In Table 4, the yields are isolated yields (Note a).

Example 5

As shown in the formula below, the amide compound 8 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester 7 (Cbz-L-Ala-OMe) comprising an amino group protected by a benzyloxycarbonyl group (Cbz) (in the amount shown in Table 5) in an atmosphere of nitrogen gas in the presence of triethylamine (Et$_3$N) (1.0 equivalent) as a base and a catalyst (10 mol %) under the temperature and reaction time conditions indicated in Table 5. The yields are shown in Table 5.

[Chem 16]

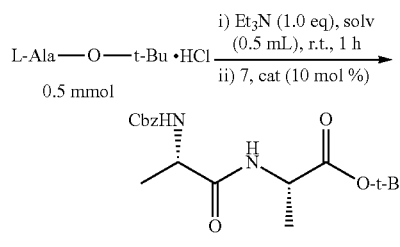

TABLE 5

| Entry | 7 (equiv) | solv. | Cat | Temp (° C.) | time(h) | yield of 8[a] (%) |
|---|---|---|---|---|---|---|
| 1 | 1.5 | none | Ta(OEt)$_5$ | 50 | 48 | 56 |
| 2 | 1.5 | none | Ta(OEt)$_5$ | 60 | 24 | 47 |
| 3 | 1.5 | none | Ta(OEt)$_5$ | 60 | 48 | 58 |
| 4 | 2.0 | none | Ta(OEt)$_5$ | 60 | 48 | 62 |
| 5 | 1.3 | none | Ta(OEt)$_5$ | 60 | 48 | 58 |
| 6 | 1.5 | none | Ta(OEt)$_5$ | 70 | 48 | 57 |
| 7 | 1.5 | none | Ta(OEt)$_5$ | 80 | 48 | 57 |
| 8 | 1.5 | none | Ta(OEt)$_5$ | 100 | 48 | 32 |
| 9 | 1.5 | none | Ta(OMe)$_5$ | 100 | 48 | 71 |
| 10 | 1.5 | n-pentane | Ta(OEt)$_5$ | 60 | 48 | 45 |
| 11 | 1.5 | c-hexane | Ta(OEt)$_5$ | 60 | 48 | 45 |
| 12 | 1.5 | toluene | Ta(OEt)$_5$ | 60 | 48 | 31 |

In Table 5, the yields are isolated yields (Note a).

Comparative Example 1

The amidation reaction was performed similarly to entry 3 in Example 5, except that no catalyst was used. As a result, the yield of the amide compound shown in Formula 8 above was 3%.

Example 6

As shown in the formula below, the amide compound 10 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester 9 (Boc-L-Ala-OMe) comprising an amino group protected by a butoxycarbonyl group (Boc) (in the amount indicated in Table 6) in an atmosphere of nitrogen gas in the presence of triethylamine (Et$_3$N) (1.0 equivalent) as a base and the catalyst (10 mol %) indicated in Table 6 under the temperature and reaction time conditions indicated in Table 6. The yields are shown in Table 6.

[Chem 17]

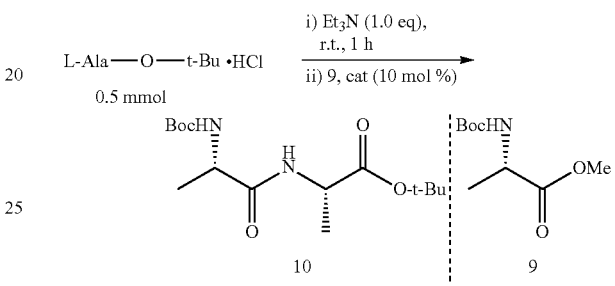

TABLE 6

| Entry | 9 (eq) | Catalyst | temp (° C.) | time (h) | yield of 10[a] (%) |
|---|---|---|---|---|---|
| 1 | 1.5 | Ta(OEt)$_5$ | 60 | 24 | 23 |
| 2 | 1.5 | Ta(OEt)$_5$ | 60 | 48 | 70 |
| 3 | 1.5 | Ta(OEt)$_5$ | 60 | 48 | 62 |
| 4 | 2.0 | Ta(OEt)$_5$ | 60 | 48 | 68 |
| 5 | 1.3 | Nb(OEt)$_5$ | 60 | 48 | 14 |
| 6 | 1.5 | Ta(OMe)$_5$ | 70 | 48 | 78 |
| 7 | 1.5 | Ta(OMe)$_5$ | 60 | 48 | 49 |
| 8 | 1.5 | Ta(OBu)$_5$ | 60 | 48 | 47 |
| 9 | 1.5 | Cu(OAc)$_2$ | 60 | 48 | 9 |
| 10 | 1.5 | Pd(OAc)$_2$ | 60 | 48 | 10 |

In Table 6, the yields are isolated yields (Note a).

Example 7

As shown in the formula below, the amide compound 10 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester (Boc-L-Ala-OMe) comprising an amino group protected by a butoxycarbonyl group (Boc) (1.5 equivalents) in an atmosphere of nitrogen gas under microwave (MW) radiation in the presence of triethylamine (Et$_3$N) as a base and Ta(OEt)$_5$ (5 to 10 mol %) as a catalyst under the temperature and reaction time conditions indicated in Table 7. The yields are shown in Table 7.

[Chem 18]

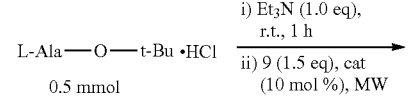

-continued

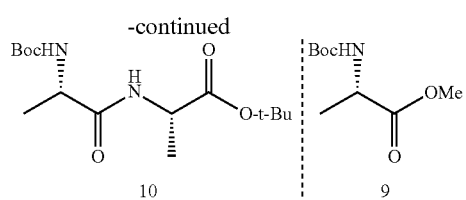

TABLE 7

| Entry | 9 (eq) | cat | solv.(mL) | temp (° C.) | time(h) | yield of 10[a] (%) |
|---|---|---|---|---|---|---|
| 1 | 1.05 | Ta(OEt)$_5$ | none | 60 | 12 | 37 |
| 2 | 1.5 | Ta(OEt)$_5$ | none | 60 | 12 | 41 |
| 3 | 1.5 | Ta(OEt)$_5$ | n-pentane (0.25) | 60 | 12 | 39 |
| 4 | 1.5 | Ta(OEt)$_5$ | none | 60 | 24 | 49 |
| 5 | 1.5 | Ta(OEt)$_5$ | none | 70 | 12 | 47 |
| 6 | 1.5 | Ta(OEt)$_5$ | Et$_2$O (0.25) | 60 | 12 | 34 |
| 7 | 1.5 | Nb(OEt)$_5$ | n-pentane (0.50) | 60 | 48 | 21 |

In Example 7, the yields are values obtained via GC analysis using octane as an internal standard (Note a).

Example 8

As shown in the formula below, the amide compound 12 (dipeptide precursor) represented by the formula below was synthesized by reacting L-alanine t-butyl ester hydrochloride (L-Ala-Ot-Bu-HCl, 0.5 mmol) as an amino compound with L-alanine methyl ester 11 (Troc-L-Ala-OMe) comprising an amino group protected by a 2,2,2-trichloroethoxycarbonyl group (Troc) (1.5 equivalents) in an atmosphere of nitrogen gas in the presence of triethylamine (Et$_3$N) as a base and Ta(OEt)$_5$ (5 to 10 mol %) as a catalyst under the temperature and reaction time conditions indicated in Table 8. The yields are shown in Table 8.

[Chem 19]

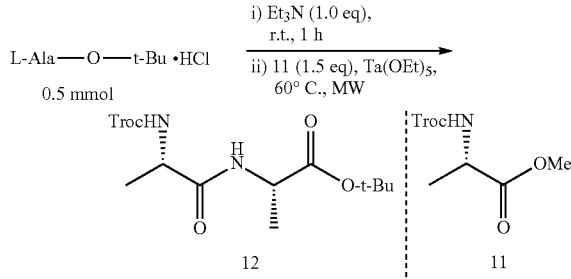

TABLE 8

| Entry | 11 (eq) | Ta(OEt)$_5$ (mol %) | solv. (mL) | MW | time(h) | yield of 12[a] (%) |
|---|---|---|---|---|---|---|
| 1 | 1.5 | 10 | none | w/o | 48 | 30 |
| 2 | 1.3 | 10 | none | w/o | 48 | 30 |
| 3 | 1.1 | 10 | none | w/o | 48 | 27 |
| 4 | 1.5 | 5 | none | w/o | 48 | 41 |
| 5 | 1.5 | 10 | none | w/o | 24 | 31 |
| 6 | 1.5 | 10 | none | w/ | 12 | 42 |
| 7 | 1.5 | 10 | n-pentane (0.25) | w/ | 24 | 38 |

In Table 8, the yields are isolated yields (Note a).

Example 9

As shown in the formula below, the amide compound (dipeptide precursor) represented by the formula below was synthesized (60% yield) by reacting L-alanine t-butyl ester hydrochloride (L-Ala-Ot-Bu-HCl, 0.5 mmol) as an amino compound with L-alanine methyl ester (Phth-L-Ala-OMe) comprising an amino group protected by a phthaloyl group (Phth) (1.5 equivalents) in an atmosphere of nitrogen gas in the presence of triethylamine (Et$_3$N) as a base and Ta(OEt)$_5$ (10 mol %) as a catalyst at a temperature of 60° C. for 24 hours.

[Chem 20]

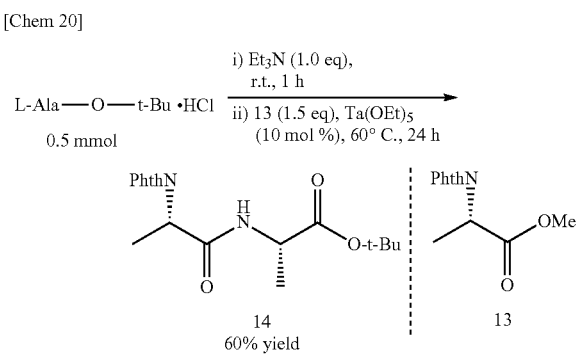

Example 10

Deprotecting reactions were performed on the protecting groups (Cbz) of various amide compounds under the following conditions in the presence of hydrogen gas. As a result, all yields were over 99% (crude).

[Chem 21-1]

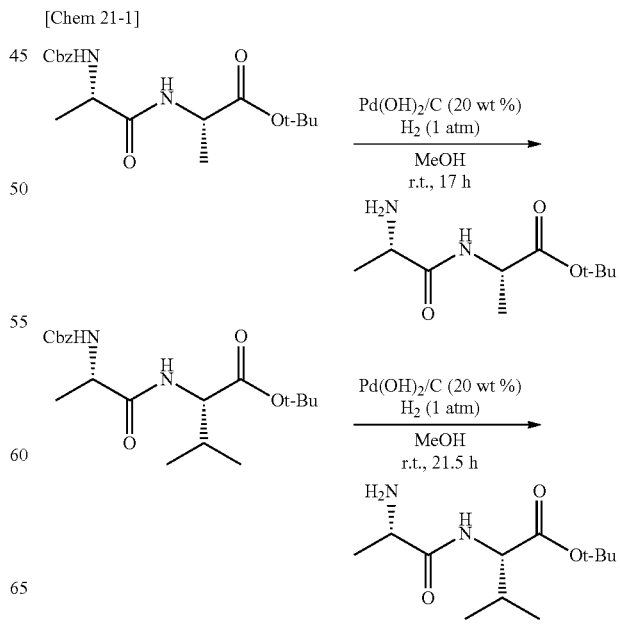

23
-continued
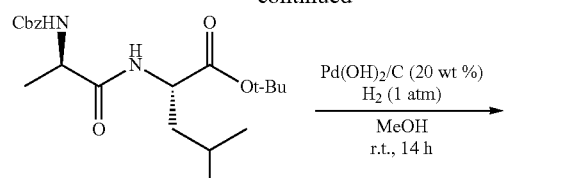
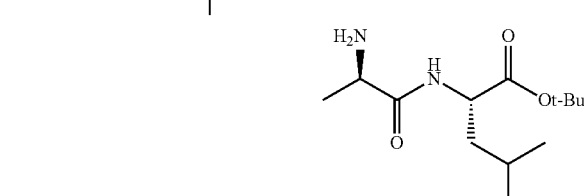
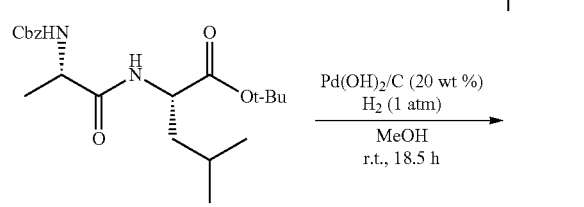
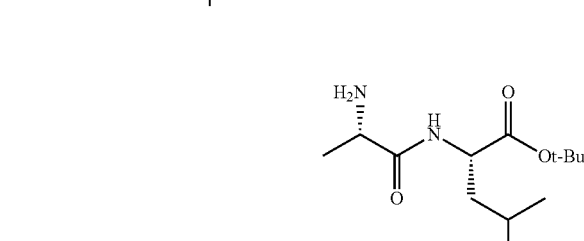
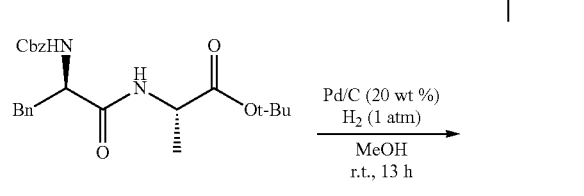
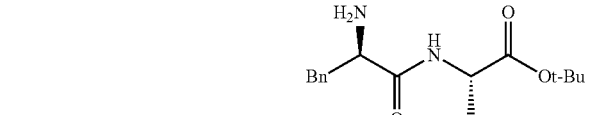
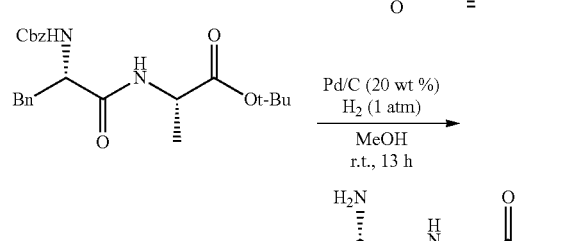
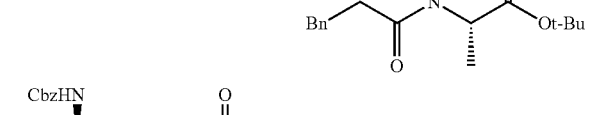
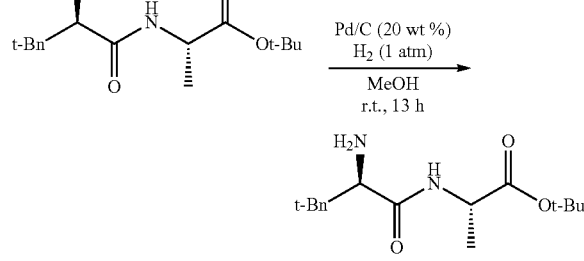
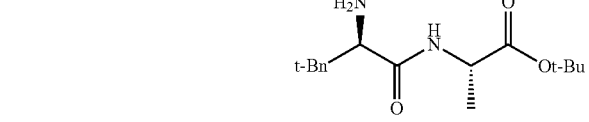
24
-continued
[Chem 21-2]
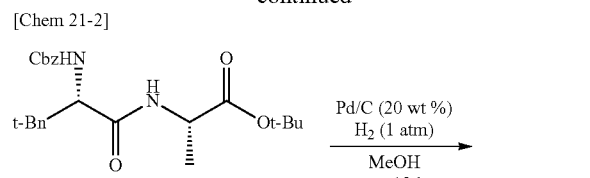
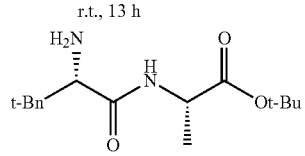
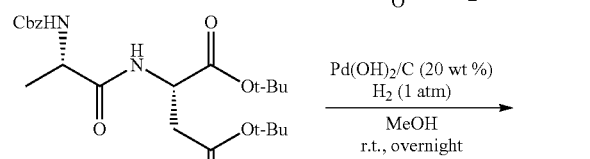
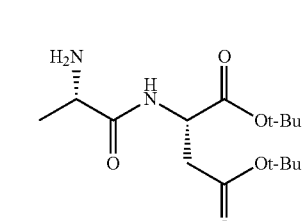
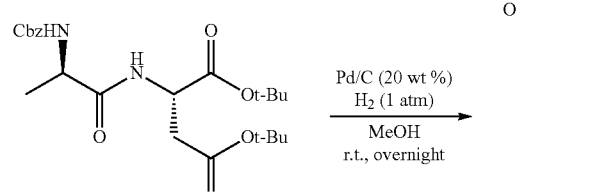
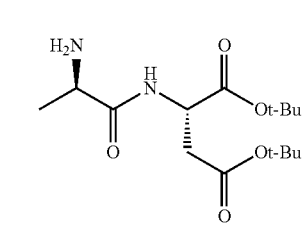
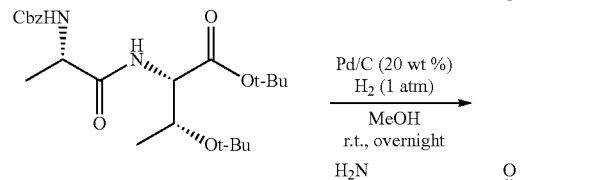
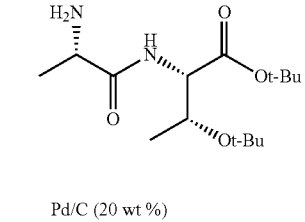
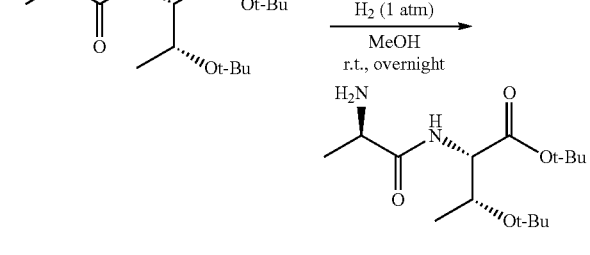
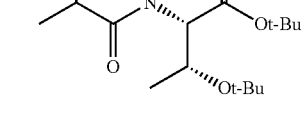

Example 11

Amide compounds were produced by reacting an aminoester compound with an amino compound under the following reaction conditions in the presence of a Ta(OMe)$_5$ catalyst and a silylating agent (TMS-imidazole). The yields are indicated along with the respective reaction conditions. In the reaction formula below, L-Ala represents an L-alanine residue, L-Ile represents an L-isoleucine residue, L-Phe represents an L-phenylalanine residue, L-Leu represents an L-leucine residue, and L-Val represents an L-valine residue.

[Chem 22]

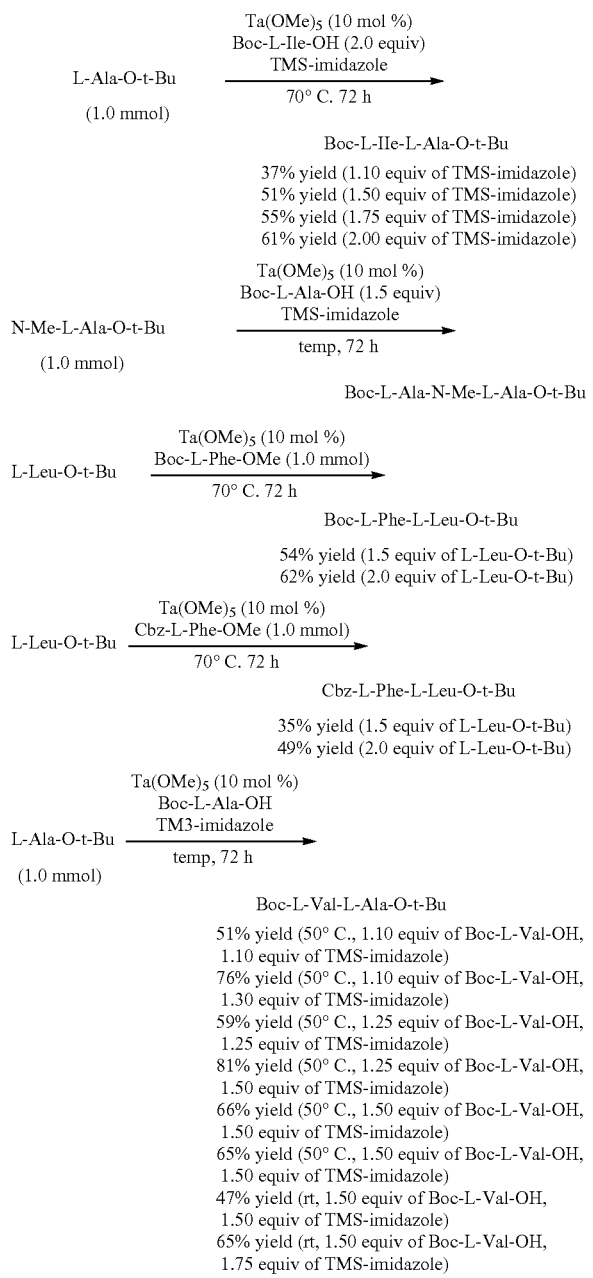

In Example 11, the yields are isolated yields. The diastereoselectivity is the value obtained by $^1$H-NMR analysis.

Example 12

Amide compounds were produced by reacting an aminoester compound with an amino compound under the following reaction conditions in the presence of a Ta(OMe)$_5$ catalyst and a silylating agent (TMS-imidazole). The yields are indicated along with the respective reaction conditions. In the reaction formula below, L-Ala represents an L-alanine residue, L-Ile represents an L-isoleucine residue, L-Phe represents an L-phenylalanine residue, and L-Leu represents an L-leucine residue. Additionally, Boc-L-Tle-OH represents N-(tert-butoxycarbonyl)-L-tert-leucine.

[Chem 23]

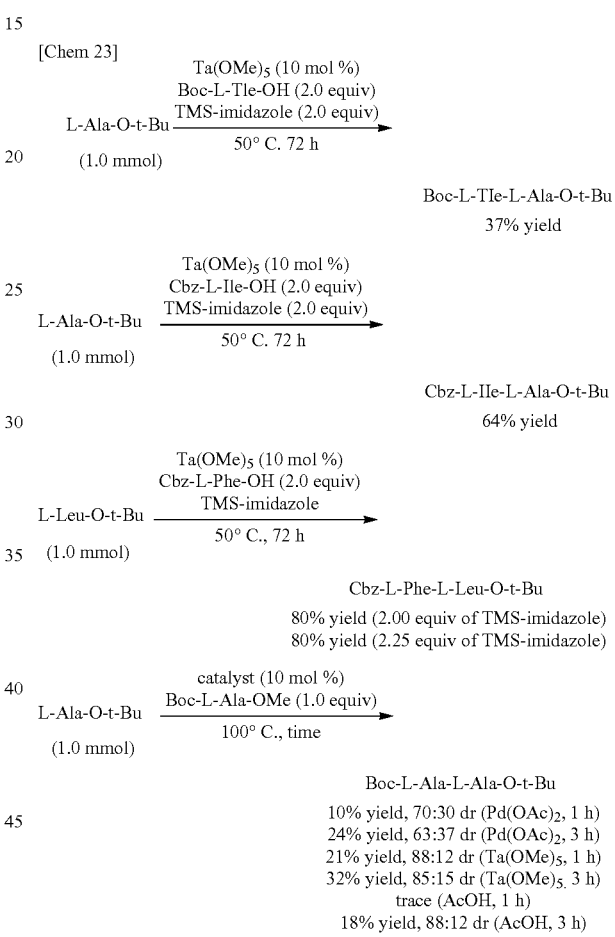

In Example 12, the yields are isolated yields. The diastereoselectivity is the value obtained by $^1$H-NMR analysis.

Example 13

Amide compounds were produced by reacting an aminoester compound with an amino compound under the respective reaction conditions below in the presence of a Ta(OMe)$_5$ catalyst and the respective types of ligand. The yield for each ligand is indicated below the reaction formula. The yield when a ligand was not used was 41%. In the following reaction formula, L-Ala represents an L-alanine residue. Additionally, Boc-(L-Ala)$_2$-OMe represents N-(tert-butoxycarbonyl)-L-alanine-L-alanine-methyl ester.

[Chem 24]

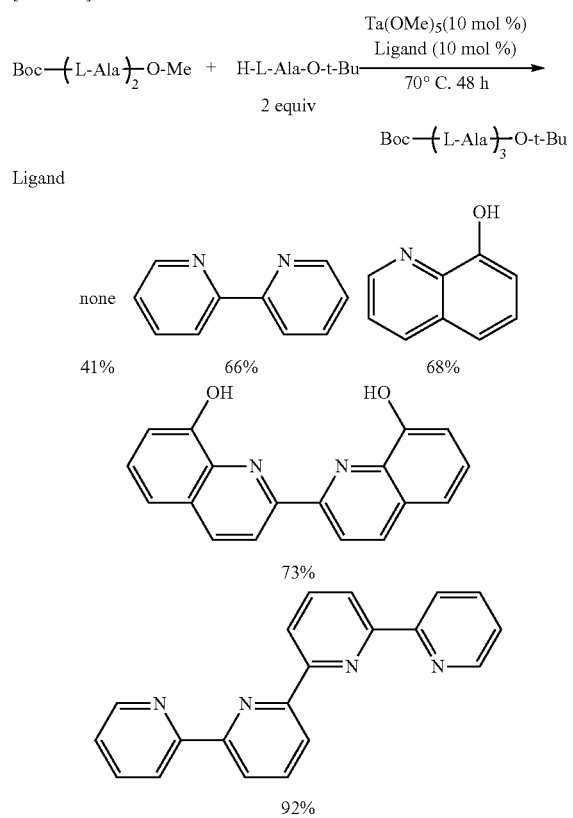

In Example 13, the yields are isolated yields.

Exercise 14

Amide compounds were produced by reacting an aminoester compound with an amino compound under the respective reaction conditions below in the presence of a Ta(OMe)₅ catalyst and a ligand. The yield for each product is indicated below the formula. In the reaction formula below, L-ala represents an L-alanine residue, Val represents an L-valine residue, Leu represents an L-Leucine residue, ILe represents an L-isoleucine residue, Gly represents glycine residue, Phe represents an L-phenylalanine residue, and Thr(OtBu) represents O-(tert butyl) L-threonine residue.

[Chem 25]

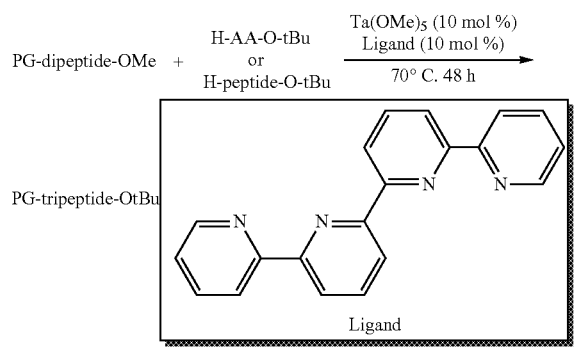

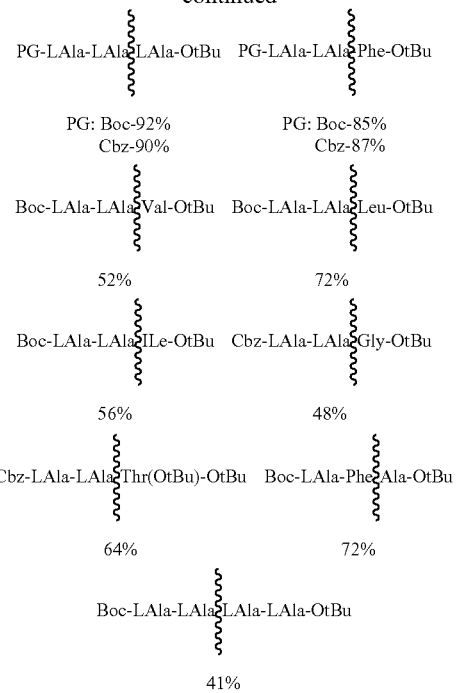

In Example 14, the yields are isolated yields.

Example 15

Amide compounds were produced by reacting an amino carboxylic acid compound with an amino compound under the respective reaction conditions below in the presence of a titanium catalyst (Cp$_2$TiCl$_2$ or (i-PrO)$_2$TiCl$_2$) and a silylating agent (TMS-imidazole). In the following reaction formula, L-Gly represents an L-glycine residue, L-Leu represents an L-Leucine residue, and L-Phe represents an L-Phenylalanine residue.

[Chem 26]

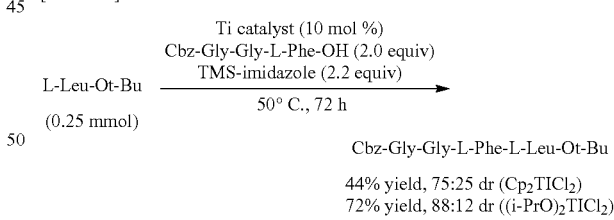

In Example 15, the yields are isolated yields. The diastereoselectivity is the value obtained by $^1$H-NMR analysis.

Example 16

Amide compounds were produced by reacting an aminoester compound with an amino compound under the respective reaction conditions below in the presence of a Pd(OAc)$_2$ catalyst and the respective types of ligand. The yield for each ligand is indicated in Table 9 below the reaction formula. Additionally, the yield when a ligand was not used was 35%.

[Chem 27]

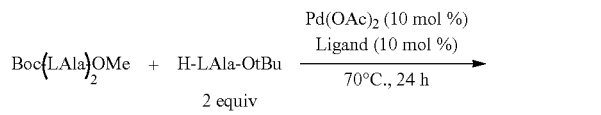

TABLE 9

| Ligand | Yield (%) |
| --- | --- |
| none | 35 |
| terpyridine | 39 |
| bipyridine | 20 |
| phenanthroline | 25 |
| TMEDA | 11 |
| PPh₃ | 23 |
| biphenyl-diol | 9 |

In Table 9, the yields are isolated yields.

Example 17

Amide compounds were produced by reacting an aminoester compound with an amino compound under the respective reaction conditions below in the presence of each type of catalyst. The yield for each catalyst is indicated in Table 10 below the reaction formula.

[Chem 28]

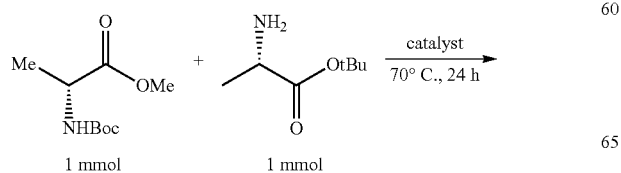

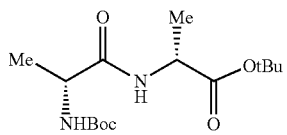

TABLE 10

| catalyst | Catalyst [mol %] | Isolated yield [%] | dr |
| --- | --- | --- | --- |
| none | — | 0 | — |
| Pd(OAc)₂ | 20 | 29 | 41:59 |
| Mn(OAc)₂ | 20 | 31 | 41:59 |
| Cu(OAc)₂ | 20 | 25 | 40:60 |
| Pb(OAc)₅ | 20 | 18 | 33:67 |
| Sn(OAc)₄ | 20 | 27 | 15:85 |
| Tl(OAc)₃ | 20 | 23 | 42:58 |
| Mg(OAc)₂·4H₂O | 20 | 17 | 28:72 |
| MgBu₂ | 20 | 15 | 47:53 |
| Ta(OMe)₅ | 10 | 51 | 1:99 |
| W(OEt)₅ | 20 | 8 | 9:91 |
| Al(O_r-Pr)₃ | 20 | 31 | 4:96 |
| Al(O_s-Bu)₃ | 20 | 25 | 4:96 |
| Al(O_t-Bu)₃ | 20 | 31 | 6:94 |

In Table 10, the yields are isolated yields. The diastereoselectivity is the value obtained by $^1$H-NMR analysis.

Example 18

Various amide compounds were produced by reacting an aminoester compound with each amino compound under the respective reaction conditions below in the presence of a Ta(Ome)₅ catalyst. The yield for each product is indicated below the reaction formula.

[Chem 29]

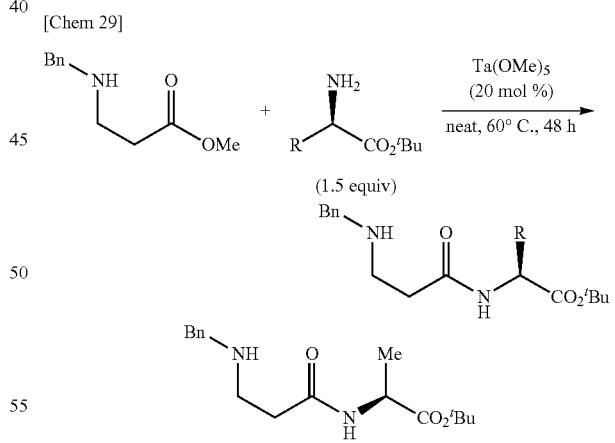

Bn-β-Ala-L-Ala-O^tBu
95% yield

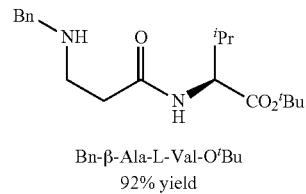

Bn-β-Ala-L-Val-O^tBu
92% yield

-continued

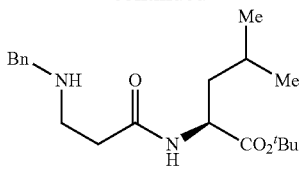

Bn-β-Ala-L-Leu-O$^t$Bu
91% yield

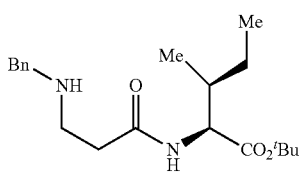

Bn-β-Ala-L-Ile-O$^t$Bu
93% yield

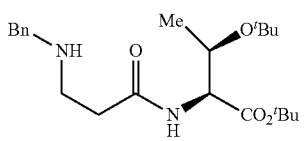

Bn-β-Ala-L-Thr(O$^t$Bu)-O$^t$Bu
75% yield

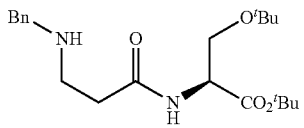

Bn-β-Ala-L-Ser(O$^t$Bu)-O$^t$Bu
81% yield

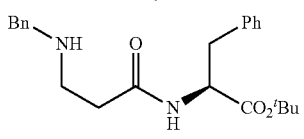

Bn-β-Ala-L-Phe-O$^t$Bu
82% yield

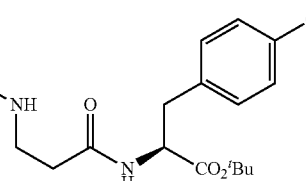

Bn-β-Ala-L-Tyr(O$^t$Bu)-O$^t$Bu
87% yield

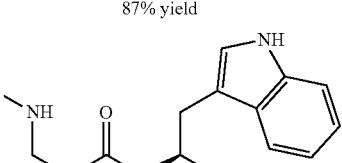

Bn-β-Ala-L-Trp-O$^t$Bu
87% yield

-continued

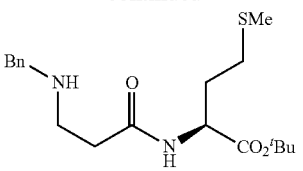

Bn-β-Ala-L-Met-O$^t$Bu
73% yield

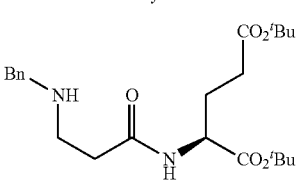

Bn-β-Ala-L-Glu(O$^t$Bu)-O$^t$Bu
72% yield

In Example 18, the yields are isolated yields.

Example 19

Various amide compounds were produced by reacting an aminoester compound with various amino compounds under the respective reaction conditions below in the presence of a Ta(Ome)$_5$ catalyst. The yield for each product is indicated below the reaction formula.

[Chem 30]

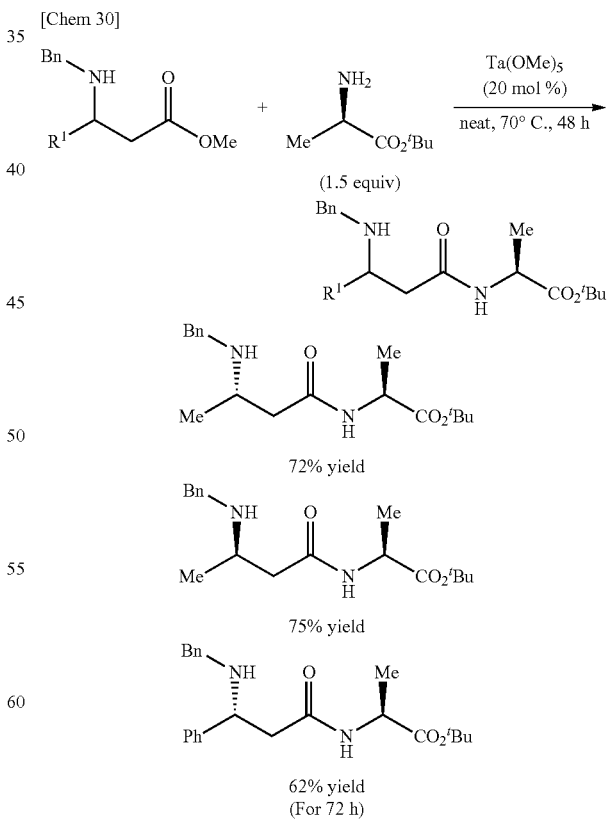

In Example 19, the yields are isolated yields.

Example 20

Various amide compounds were produced by reacting an aminoester compound with various amino compounds under the respective reaction conditions below in the presence of a Ta(OMe)₅ catalyst. The yield for each product is indicated below the reaction formula.

[Chem 31]

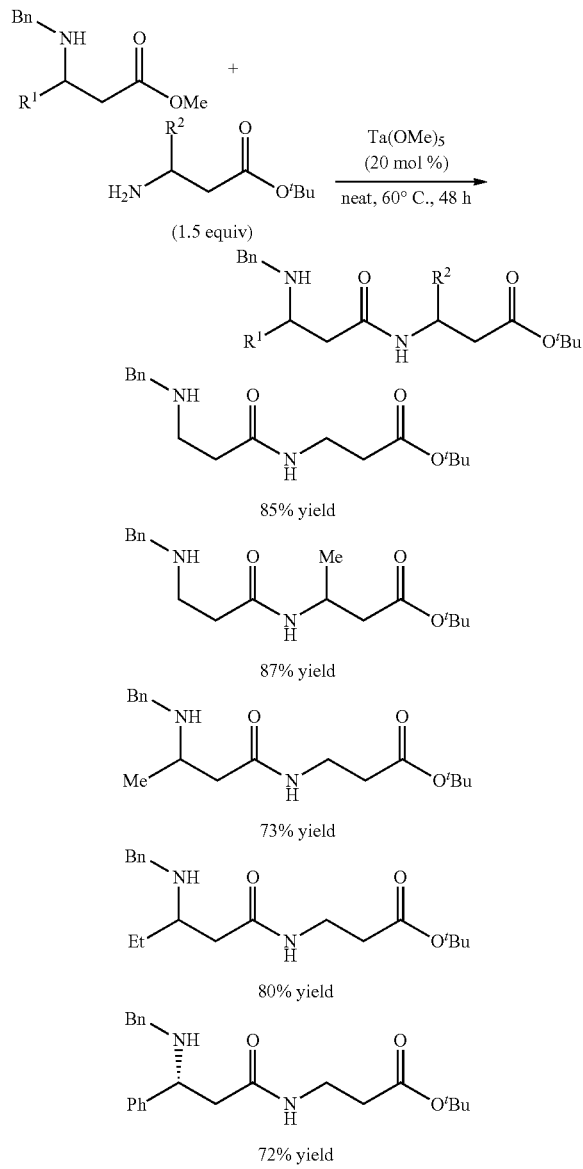

In Example 20, the yields are isolated yields.

The invention claimed is:

1. A method for producing an amide compound, comprising an amidation step for reacting, in the presence of a Lewis acid catalyst comprising at least one metal selected from tantalum, tungsten, niobium, neodymium, iron, silver, and palladium, an amino compound with an aminoester compound represented by general formula (1) below to amidate the ester group in the aminoester compound:

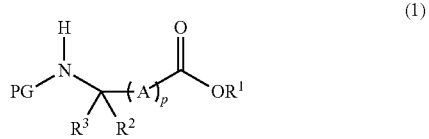

where group $R^1$ represents an optionally substituted aliphatic group, an optionally substituted aromatic group, an optionally substituted alicyclic group, or an optionally substituted heterocyclic group, group $R^2$ and group $R^3$ each independently represent a hydrogen atom, a halogen atom, a hydroxyl group, an optionally substituted aliphatic group, an optionally substituted aromatic group, an optionally substituted alicyclic group, or an optionally substituted heterocyclic group, group PG represents an amino group-protecting group, A represents a linear or branched optionally substituted alkyl group having 1 to 3 carbon atoms, and p is 0 or 1;

wherein the Lewis acid catalyst has a formula selected from: $TaX_5$, $WX_5$, $NbX_5$, $NdX_3$, $FeX_2$, $AgX$, and $PdX_2$, and X is selected from fluorine, chlorine, bromine, iodine, alkoxy, acetylacetonato (acac), acetoxy (AcO), cyclopentadienyl (Cp), and trifluoromethanesulfonato (TfO).

2. The method for producing an amide compound according to claim 1, further comprising a deprotection step wherein after the amidation step, in the obtained amide compound, the protecting group PG derived from the aminoester compound represented by general formula (1) is deprotected to obtain a converted amino group.

3. The method for producing an amide compound according to claim 2, further comprising an amidation step for reacting, in the presence of the Lewis acid catalyst, an amide compound having the amino group obtained in claim 2 with an aminoester compound represented by general formula (1) to amidate the ester group of the aminoester compound.

4. The method for producing an amide compound according to claim 1, wherein the group PG is a tert-butoxycarbonyl group (Boc), benzyl group (Bn), benzyloxycarbonyl group (Cbz), benzoyl group (Bz), 2,2,2-trichloroethoxycarbonyl group (Troc), allyloxycarbonyl group (Alloc), 2,4-dinitrophenyl group (2,4-DNP), phthaloyl group (Phth), paramethoxy benzoyl group (PMPCO), cinnamoyl group, toluene sulfonyl group (Ts), 2- or 4-nitrobenzene sulfonyl group (Ns), or 9-fluorenyl methyloxycarbonyl group (Fmoc).

5. The method for producing an amide compound according to claim 1, wherein the amino compound is an amino compound represented by general formula (3) below:

where group $R^a$ and group $R^b$ each independently represent a hydrogen atom, an optionally substituted aliphatic group, an optionally substituted aromatic group, an optionally substituted alicyclic group, or an optionally substituted heterocyclic group, or group $R^a$ and group $R^b$ may form, along with a bonding nitrogen atom, a saturated or unsaturated heterocyclic ring, and the heterocyclic ring may have a substituent.

6. A method for producing an amide compound, comprising an amidation step for reacting, in the presence of a Lewis acid catalyst comprising at least one metal selected from titanium, tantalum, tungsten, hafnium, niobium, neodymium, iron, copper, silver, and palladium, an amino compound with an aminoester compound represented by general formula (1) below to amidate the ester group in the aminoester compound:

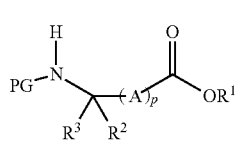

(1)

where group $R^1$ represents an optionally substituted aliphatic group, an optionally substituted aromatic group, an optionally substituted alicyclic group, or an optionally substituted heterocyclic group, group $R^2$ and group $R^3$ each independently represent a hydrogen atom, a halogen atom, a hydroxyl group, an optionally substituted aliphatic group, an optionally substituted aromatic group, an optionally substituted alicyclic group, or an optionally substituted heterocyclic group, group PG represents an amino group-protecting group, A represents a linear or branched optionally substituted alkyl group having 1 to 3 carbon atoms, and p is 0 or 1;

wherein the Lewis acid catalyst has a formula selected from: $TiX_4$, $TaX_5$, $WX_5$, $HfX_4$, $NbX_5$, $NdX_3$, $FeX_2$, $CuX_2$, $AgX$, and $PdX_2$, and X is selected from fluorine, chlorine, bromine, iodine, alkoxy, acetylacetonato (acac), acetoxy (AcO), cyclopentadienyl (Cp), and trifluoromethanesulfonato (TfO), wherein the amino compound is an amino acid or a salt thereof, or an amino acid ester or a salt thereof.

7. The method for producing an amide compound according to claim 1, wherein the amount of the catalyst used is not more than 20 mol % based on 100 mol % of the aminoester compound.

8. The method for producing an amide compound according to claim 1, wherein the amidation reaction is performed in the presence of a base.

9. The method for producing an amide compound according to claim 1, wherein the amide compound obtained from the amidation reaction is represented by general formula (4) below:

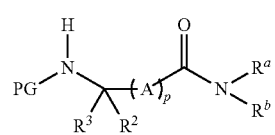

(4)

where group $R^2$, group $R^3$, and PG are each the same as in general formula (1) above, group $R^a$ and group $R^b$ each independently represent a hydrogen atom, an optionally substituted aliphatic group, an optionally substituted aromatic group, an optionally substituted alicyclic group, or an optionally substituted heterocyclic group, or group $R^a$ and group $R^b$ may form, along with a bonding nitrogen atom, a saturated or unsaturated heterocyclic ring, the heterocyclic ring may have a substituent, A represents a linear or branched optionally substituted alkyl group having 1 to 3 carbon atoms, and p is 0 or 1.

10. The method for producing an amide compound according to claim 6, wherein the group PG is a tert-butoxycarbonyl group (Boc), benzyl group (Bn), benzyloxycarbonyl group (Cbz), benzoyl group (Bz), 2,2,2-trichloroethoxycarbonyl group (Troc), allyloxycarbonyl group (Alloc), 2,4-dinitrophenyl group (2,4-DNP), phthaloyl group (Phth), paramethoxy benzoyl group (PMPCO), cinnamoyl group, toluene sulfonyl group (Ts), 2- or 4-nitrobenzene sulfonyl group (Ns), or 9-fluorenyl methyloxycarbonyl group (Fmoc).

* * * * *